United States Patent [19]

Nagubandi

[11] Patent Number: 4,548,759
[45] Date of Patent: Oct. 22, 1985

[54] PREPARATION OF PHOSPHONOMETHYLATED AMINO ACIDS

[75] Inventor: Sreeramulu Nagubandi, New City, N.Y.

[73] Assignee: Stauffer Chemical Company, Westport, Conn.

[21] Appl. No.: 645,735

[22] Filed: Aug. 30, 1984

[51] Int. Cl.[4] ............................................. C07F 9/38
[52] U.S. Cl. ........................ 260/502.5 F; 260/456 A
[58] Field of Search ................................. 260/502.5 F

[56] References Cited

U.S. PATENT DOCUMENTS

| 2,609,390 | 9/1952 | Bersworth | 260/502.5 F |
| 3,288,846 | 11/1966 | Irani et al. | 260/502.5 F |
| 3,977,860 | 8/1976 | Franz | 260/502.5 F |
| 4,422,982 | 12/1983 | Subramian | 260/502.5 F |
| 4,439,373 | 3/1984 | Nagubandi | 260/502.5 F |
| 4,457,873 | 7/1984 | Nagubandi | 260/502.5 F |
| 4,491,548 | 1/1985 | Nagubandi | 260/502.5 F |

FOREIGN PATENT DOCUMENTS 1413137 11/1975 United Kingdom .

Primary Examiner—J. E. Evans
Attorney, Agent, or Firm—Hensley M. Flash

[57] ABSTRACT

A process for preparing phosphonomethylated amino acids comprising reacting a glycine derivative with a halosulfonic acid to form a N-sulfonylglycine derivative, then phosphonomethylating the N-sulfonylglycine derivative with formaldehyde and a phosphorus source to obtain a phosphonomethylated N-sulfonylglycine derivative which is then hydrolyzed to the corresponding phosphonomethylated amino acid, e.g. glyphosate or the acid derivative.

9 Claims, No Drawings

PREPARATION OF PHOSPHONOMETHYLATED AMINO ACIDS

BACKGROUND OF THE INVENTION

1. Field of the Invention

The present invention is a process for preparing phosphonomethylated amino acids, and in particular, for preparing N-phosphonomethylglycine, otherwise known as glyphosate.

2. Related Information

Certain phosphonomethylated amino acids, e.g. glyphosate and its derivatives, are herbicides. Herbicides are useful for controlling or modifying plant growth. Glyphosate and its derivatives are effective in controlling or modifying growth in a wide variety of plant species, including broadleaves, grasses and sedge.

Because glyphosate and its derivatives are so important, new processes for making it and its derivatives faster, cheaper or in greater yields are constantly in demand. A new process for preparing glyphosate and its derivatives has now been discovered.

U.S. Pat. No. 4,439,373 (Nagubandi, Mar. 27, 1984) discloses a process for preparing phosphonomethylated amino acids by reacting a primary amino acid ester or salt with a carbon dioxide group to form a glycine carbamate compound then phosphonomethylating said amino compound to obtain a phosphonomethylated amino compound and acidifying said phosphonomethylated amino compound to expel carbon dioxide and yield a phosphonomethylated amino acid or acid derivative.

British Patent No. 1,413,137 (Beauhaire et al., Nov. 5, 1975) generally discloses using an emulsifiable oil in a process for the cold rolling of light metals. The reference specifically discloses the use of sodium and triethanol amine sulfur amido acetate in this process.

A process for preparing a phosphonomethylated amino acid by first forming an N-sulfonylglycine derivative then phosphonomethylating said derivative then further hydrolyzing the resulting product to obtain the phosphonomethylated amino acid would be advantageous.

It is an object of the present invention to provide a process for preparing phosphonomethylated amino acids.

Other objects and advantages of the present invention are shown throughout the specification.

SUMMARY OF THE INVENTION

In accordance with the present invention it has now been discovered that a phosphonomethylated amino acid can be prepared by a process comprising: (a) reacting a glycine derivative with a halosulfonic acid to form a N-sulfonylglycine derivative; (b) phosphonomethylating said N-sulfonylglycine derivative to obtain a phosphonomethylated N-sulfonylglycine derivative; and (c) hydrolyzing said phosphonomethylated N-sulfonylglycine derivative to obtain a phosphonomethylated amino acid or acid derivative. The N-sulfonylglycine derivative is phosphonomethylated at the nitrogen.

The process is illustrated by the preparation of glyphosate or its derivatives, however other phosphonomethylated amino acids or their derivatives can be prepared by the process. In one preferred embodiment, the process comprises: (a) reacting glycine with chlorosulfonic acid in the presence of a base and at a temperature range of from about 0° C. to about 10° C. to form a N-sulfonylglycine derivative; (b) phosphonomethylating said N-sulfonylglycine derivative by reaction with formaldehyde and phosphorous acid in the presence of a solvent and with refluxing from about 1 to about 3 hours; and (c) hydrolyzing said phosphonomethylated N-sulfonylglycine derivative by refluxing in the presence of a strong acid to form glyphosate.

DETAILED DESCRIPTION OF THE INVENTION

The present invention comprises a process for preparing phosphonomethylated amino acids. In this process, a glycine derivative is reacted with a halosulfonic acid to form a N-sulfonylglycine derivative which is then phosphonomethylated with the resulting product being hydrolyzed to obtain a phosphonomethylated amino acid or acid derivative.

The following reactions illustrate the present invention:

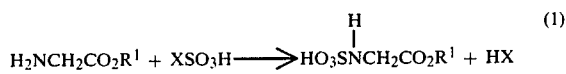

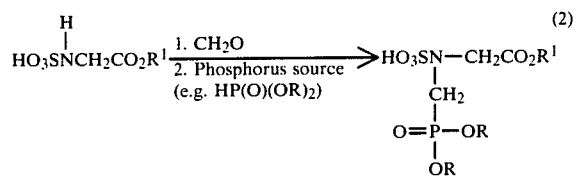

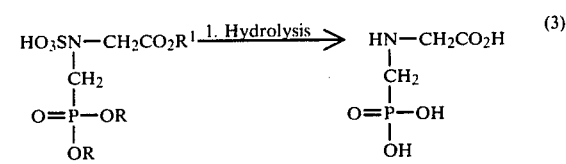

In reaction (1) a glycine derivative is reacted with a halosulfonic acid to form an N-sulfonylglycine derivative.

In reaction (2) the N-sulfonylglycine derivative is phosphonomethylated at the nitrogen using formaldehyde and a phosphorus source.

In reaction (3) the phosphonomethylated N-sulfonylglycine derivative is hydrolyzed to obtain a phosphonomethylated amino acid.

In reaction (1), X is a halide selected from the group consisting of chloride, bromide and iodide. In reaction (1), (2) and (3), $R^1$ is selected from the group consisting of hydrogen and alkyl having 1 to 4 carbon atoms. A preferred halosulfonic acid is chlorosulfonic acid.

Reaction (1) preferably takes place in the presence of a suitable base. Suitable bases can include, for example, sodium hydroxide, sodium bicarbonate, sodium carbonate, pyridine and triethylamine.

It is desirable to carry out reaction (1) at or below room temperature, with a temperature range of from about 0° C. to about 10° C. being preferable. The molar ratio of the glycine derivative to the halosulfonic acid can generally range from about a 1:3 ratio, with about a 1:2 ratio being desirable and about a 1:1 molar ratio being preferable.

The particular N-sulfonylglycine derivative resulting from reaction (1) will vary according to the specific glycine derivative, halosulfonic acid and base used. For example, when the preferred chlorosulfonic acid is reacted with glycine in the presence of sodium hydroxide, NaO₃SN(H)CH₂CO₂Na results. In this application, N-sulfonylglycine and its derivatives are characterized as the N-sulfonylglycine derivative.

The N-sulfonylglycine derivative can be separated from the reaction mixture by filtration. Acidification with, for example, concentrated hydrochloric acid can convert the derivative into N-sulfonylglycine. The recovery of N-sulfonylglycine can be aided by the use of a solvent, for example ethanol, and the recovered product can be washed with, for example, diethylether to enhance the purity of the product.

The phosphorus source used in reaction (2) is selected from the group consisting of:

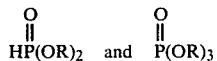

wherein R is selected independently each time it occurs from the group consisting of hydrogen, alkyl having 1 to 8 carbon atoms, inclusive; phenyl and substituted phenyl wherein the substituents are selected from the group consisting of alkyl having 1 to 4 carbon atoms, inclusive; alkoxy having 1 to 4 carbon atoms, inclusive; and halogen. A preferred phosphorus source is phosphorous acid.

In reaction (2) the formaldehyde used can be in the form of aqueous formaldehyde or solid paraformaldehyde. If solid paraformaldehyde is used, water can be used as a solvent. The mole ratio of formaldehyde to the N-sulfonylglycine derivative should be at least 1:1. Excess amount of formaldehyde, up to a 3:1 mole ratio can be employed. Mole ratios greater than 3:1 are not desirable for economic reasons.

The N-sulfonylglycine derivative can be suspended in an organic solvent such as methanol. If this is done, it may be necessary to make the reaction mixture basic with a suitable base before adding formaldehyde to the protected amino compound. Suitable bases include but are not limited to sodium hydroxide, sodium methoxide and sodium ethoxide.

The phosphorus source can then be added to the reaction mixture. The mole ratio of the phosphorus source to the N-sulfonylglycine derivative should also be at least 1:1 and can range up to about 2:1. Greater amounts of the phosphorus source relative to the N-sulfonylglycine derivative are not economically desirable.

After the addition of the phosphorus source, the resulting reaction mixture is heated to reflux from about 80° C. to about 100° C. for at least 2 to 3 hours. A phosphonomethylated N-sulfonylglycine derivative results. This derivative can be separated by filtration.

In reaction (3) a phosphonomethylated N-sulfonylglycine derivative is hydrolyzed to prepare the desired phosphonomethylated amino acid or acid derivative. In this hydrolysis reaction, the derivative is heated preferably to reflux temperature in the presence of a suitable strong acid. Generally, a range of from about 4 moles to about 15 moles of acid can be used, with from about 4 moles to about 10 moles being desirable and about 4 moles to about 6 moles being preferable. Typically, at reflux temperatures, the reaction time ranges from about 1 hour to about 10 hours, with about 1 hour to above 5 hours being desirable and about 2 hours to about 3 hours being preferable. Suitable strong acids include, but are not limited to, hydrochloric acid, sulfuric acid and nitric acid. After refluxing, evaporation of the solvent yields a phosphonomethylated amino acid or acid derivative.

The following examples describe various embodiments of the invention. Other embodiments will be apparent to the skilled in the art from a consideration of the specification or practice of the invention disclosed herein. It is intended that the specifications and examples be considered as exemplary only, with the true scope and spirit of the invention being indicated by the claims which follow the examples.

EXAMPLE 1

Synthesis of N-Sulfonylglycine

Glycine (10.0 grams, 0.133 mole) was suspended in dry toluene (50 mls) and triethylamine (26.95 grams, 0.266 mole). This suspension was cooled in an ice bath then chlorosulfonic acid (15.5 grams, 0.133 moles) was slowly added under a nitrogen atmosphere. This reaction mixture was then stirred for about 50 hours. After the first 2 hours of strirring the resulting fuming subsided.

The resulting triethylamine hydrochloride precipitate was separated by filtration, then the filtrate was concentrated to yield a white solid, N-sulfonylglycine, which was used in the other steps of the process of this invention. The N-sulfonylglycine was identified using NMR and IR and the yield was 60% by weight.

EXAMPLE 2

Synthesis of Glyphosate via N-Sulfonylglycine

N-sulfonylglycine (5 grams, 0.032 mole), prepared in the prior Example was suspended in methanol (50 mls) and sodium methoxide (25% sodium hydroxide in methanol) was added to adjust the pH of the suspension to 8-9. Paraformaldehyde (1 gram, 0.033 mole) and trimethylphosphite (3.8 mls, 0.032 moles) were added to the suspension and the resulting reaction mixture was then refluxed. The pH was adjusted with sodium methoxide solution from time to time to maintain it between 8 and 9. After 5 hours, the solids present in the reaction mixture were separated and the filtrate was evaporated. The resulting residue was refluxed with concentrated HCl (25 mls). After 3 hours, the solvent was removed to obtain the product glyphosate. This product was isolated and the structure confirmed by H and ³¹P NMR spectroscopy.

What is claimed is:
1. A process for preparing a phosphonomethylated amino acid comprising:
   (a) reacting a glycine derivative with a halosulfonic acid to form a N-sulfonylglycine derivative;
   (b) phosphonomethylating said N-sulfonylglycine derivative to obtain a phosphonomethylated N-sulfonylglycine derivative; and
   (c) hydrolyzing said phosphonomethylated N-sulfonylglycine derivative to obtain a phosphonomethylated amino acid or acid derivative.
2. The process of claim 1 wherein the reaction of step (a) is carried out in the presence of a base.
3. The process of claim 2 wherein the reaction of step (a) is carried out at a temperature of from about 0° C. to about 10° C.
4. The process of claim 1 wherein said N-sulfonylglycine derivative is phosphonomethylated by the use of formaldehyde and a phosphorus source.
5. The process of claim 1 wherein said N-sulfonylglycine derivative is phosphonomethylated by adding at least 1 mole equivalent of formaldehyde and at least 1 mole equivalent of a phosphorus source to said N-sulfonylglycine derivative to form a reaction mixture; and then refluxing said reaction mixture to obtain a phosphonomethylated N-sulfonylglycine derivative.

6. The process of claim 4 wherein said phosphorus source has the structure:

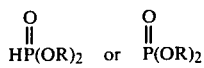

wherein R is selected independently each time it occurs from the group consisting of hydrogen, alkyl having 1 to 8 carbon atoms, inclusive; phenyl and substituted phenyl wherein the substituents are selected from the group consisting of alkyl having 1 to 4 carbon atoms, inclusive; alkoxy having 1 to 4 carbon atoms, inclusive; and halogen.

7. The process of claim 1 wherein said phosphonomethylated N-sulfonylglycine derivative is hydrolyzed in the presence of a strong acid.

8. The process of claim 7 wherein said phosphonomethylated N-sulfonylglycine derivative is hydrolyzed by refluxing for about 1 to about 3 hours in the presence of a strong acid selected from the group consisting of hydrochloric acid, sulfuric acid and nitric acid.

9. A process for preparing glyphosate comprising:
 (a) reacting glycine with chlorosulfonic acid in the presence of a base and at a temperature range of from about 0° C. to about 10° C. to form a N-sulfonylglycine derivative;
 (b) phosphonomethylating said N-sulfonylglycine derivative by reaction with formaldehyde and phosphorous acid in the the presence of a solvent and with refluxing from about 1 to about 3 hours; and
 (c) hydrolyzing said phosphonomethylated N-sulfonylglycine derivative by refluxing in the presence of a strong acid to form glyphosate.

* * * * *